United States Patent [19]

Joch et al.

[11] 4,197,252

[45] Apr. 8, 1980

[54] PROCESS FOR THE PREPARATION OF ORTHOSILICIC ACID TETRAALKOXYALKYL ESTERS

[75] Inventors: Wilhelm Joch, Niederkassel; Arnold Lenz, Cologne-Stammheim; Walter Rogler, Bonn, all of Fed. Rep. of Germany

[73] Assignee: Dynamit Nobel Aktiengesellschaft, Troisdorf, Fed. Rep. of Germany

[21] Appl. No.: 519,303

[22] Filed: Oct. 30, 1974

[30] Foreign Application Priority Data

Nov. 2, 1973 [DE] Fed. Rep. of Germany ....... 2354683

[51] Int. Cl.$^2$ .............................................. C07F 7/04
[52] U.S. Cl. .................................................... 556/446
[58] Field of Search ................................. 260/448.8 A

[56] References Cited

U.S. PATENT DOCUMENTS

| | | | |
|---|---|---|---|
| 3,627,807 | 12/1971 | Bleh et al. | ...................... 260/448.8 A |
| 3,803,197 | 4/1974 | Anderson et al. | ............ 260/448.8 A |

*Primary Examiner*—Paul F. Shaver
*Attorney, Agent, or Firm*—Sprung, Felfe, Horn, Lynch & Kramer

[57] ABSTRACT

A process for preparing an orthosilicic acid tetraester of a monoalkyl ether of an aliphatic glycol having 2 to 6 carbon atoms which comprises contacting silicon, iron silicide or ferrosilicon with a monoalkyl ether of an aliphatic glycol having 2 to 6 carbon atoms in the aliphatic chain in the presence of the corresponding orthosilicic acid tetraalkoxy alkyl ether at a temperature between 125 and 250° C.

11 Claims, No Drawings

PROCESS FOR THE PREPARATION OF ORTHOSILICIC ACID TETRAALKOXYALKYL ESTERS

BACKGROUND OF THE INVENTION

1. Field of the Invention

This invention relates particularly to the preparation of orthosilicic acid tetraesters of monoalkyl ethers of an aliphatic glycol, particularly to orthosilicic acid tetraalkoxyalkyl esters having 2 to 6 carbon atoms in the main chain and 1 to 4 carbon atoms in the chain of the monoalkyl ether. This invention is particularly directed to a process for the production of such orthosilicic acid tetraalkoxyalkyl esters which can be carried out at an exceptionally high volume-time yield, such as a volume-time yield equal to or better than the volume-time yields obtained in the preparation of orthosilicic acid tetraalkyl esters from simple alcohols.

2. Discussion of the Prior Art

It is known to prepare orthosilicic acid tetraalkylesters by the reaction of silicon, iron silicide or ferrosilicon with alcohol in the presence of the corresponding alcoholate which process is carried out in the presence of 70 to 99 weight percent of the corresponding orthosilicic acid tetraalkyl ester. The process is carried out such that the alcohol which forms such ester on reaction with the silicon containing compound is continuously added to the reaction mixture. The process provides good volume-time yields principally in the production of lower alkyl orthosilicic acid tetraalkyl esters. However, when the alkyl radical of the ester grouping becomes long the volume-time yield obtained by the process becomes considerably poor.

It is known in this reaction to utilize silicon of specific grain sizes as these grain sizes are known to effect the speed of formation of the ester. The reaction speed is improved when the silicon has a good ability to become wetted by the alcohol or alcoholates used in the process. In contrast to this, it is known that ether alcohols can be used as stabilizing agents for chlorinated hydrocarbons whereby the chlorinated hydrocarbon is stabilized against attack by a metal. It is also known that the surface of light metals is passivated when contacted with an ether alcohol. It has, therefore, been expected that the preparation of an orthosilicic acid tetraalkoxyalkyl ester from silicon, ferrosilicon or iron silicide using an ether alcohol would proceed quite poorly owing to the inability of the silicon to be adequately wetted by the ether alcohol. It was expected that the formation of any tetraalkoxyalkyl ether of orthosilicic acid would be obtained quite slowly.

For these reasons orthosilicic acid esters of ether alcohols have, in practice, been prepared by the transesterification of orthosilicic acid methyl esters with the corresponding ether alcohol. This process is complicated owing to the fact that a two-step process must be performed. Moreover, the process does not provide the desired high volumne-time yields such as are obtained in the preparation of orthosilicic acid tetra (lower alkyl) esters.

It, therefore, became desirable to provide a process for the preparation of such tetraalkoxyalkyl esters of orthosilicic acid whereby the desired ester could be obtained in a high volume-time yield. It became particularly desirable to provide such a process which could be carried out in one step. Moreover, it became desirable to provide such a process which could be carried out using readily available materials and did not require the assembly of an elaborate reaction vessel or system or the imposition of expensive processing parameters.

SUMMARY OF THE INVENTION

The objects of this invention are attained by a process for preparing an orthosilicic acid tetraester of a monoalkyl ether of an aliphatic glycol having 2 to 6 carbon atoms which process comprises contacting silicon, iron silicide or ferrosilicon with a monoalkyl ether of an aliphatic glycol having 2 to 6 carbon atoms in the aliphatic chain in the presence of the corresponding orthosilicic acid tetraalkoxyalkyl ester at a temperature between 125° and 250° C.

It has been surprisingly found that by using a mildly elevated temperature of at least 125° C. and up to 250° C. an orthosilicic acid tetraester of a monoalkyl ether of an aliphatic glycol can be prepared at an exceptionally high volume-time yield. The process can be carried out simply by introducing into a reaction vessel the orthosilicic acid tetraalkoxyalkyl ester that is desired to be prepared. Into such vessel there is also introduced silicon, iron silicide or ferrosilicon. Thereafter, the corresponding alcohol corresponding to the alkoxyalkyl ester, is introduced into the reaction mixture. The reaction mixture is maintained at a temperature between 125° and 250° C. High volume-time yields of the desired orthosilicic acid tetraalkoxyalkyl ester are provided.

The process is particularly desirably carried out by including in the reaction mixture an alkali metal alcoholate corresponding to the ether alcohol to be introduced into the reaction mixture. This alkali metal ether alcoholate can be formed in situ by merely introducing into the reaction vessel, before charging the same with ether alcohol, the alkali metal itself. When the ether alcohol is introduced into the reaction vessel containing the corresponding orthosilicic acid tetraalkoxyalkyl ester, silicon, iron silicide or ferrosilicon, an alkali metal, the corresponding alkali metal ether alcoholate is formed. When in such reaction mixture when in dissolved form it provides a catalytic function so that entering ether alcohol is readily formed, upon contact of the silicon-containing material into the orthosilicic acid tetraalkoxy ether.

The reaction takes place at a temperature between 125° and 250° C., preferably 140° to 225° C. The reaction is very rapid under these conditions so that the volume-time yields are at least equal to and in many instances greater than the volume-time yields obtained for the corresponding preparation of orthosilicic acid tetramethyl esters as described in West German Pat. No. 1,793,222.

For ease in understanding the amount of reactants employed there is set forth below a table showing the broad and preferred ranges for the preparation of the tetraalkoxyalkyl esters it being understood that temperature considerations are important in the subject process in obtaining the desired high volume-time yields.

TABLE I

| Component | Percent by Weight of Reactants | |
|---|---|---|
| | Broad | Preferred |
| Orthosilicic acid tetra-alkoxyalkyl ester | 28 to 98 | 35 to 95 |
| Silicon, iron silicide or ferrosilicon | 1 to 80 | 40 to 60 |
| Monoalkyl ether of | 1 to 30 | 5 to 15 |

TABLE I-continued

| | Percent by Weight of Reactants | |
|---|---|---|
| Component | Broad | Preferred |
| aliphatic glycol | | |

For the achievement of the good volume-time yields it is important to stay within the temperature limits of the invention. In the preparation of orthosilicic acid tetraalkoxyalkyl esters having a low ester grouping, such as for example the methoxy ethyl or ethoxy ethyl ester, it is preferable to operate in the lower part of the above-stated temperature range. The more carbon atoms the alkoxyalkyl ester has, the higher will be the preferred reaction temperature. The upper temperature limit of 225° C. may not be exceeded in the preparation of pure products (purity greater than 95%), because then the silicic acid ester will be contaminated by by-product formation.

The silicon to be used is preferably silicon of a purity greater than 98%. One can also use ferrosilicon or iron silicide as the silicon-containing component. The ester that forms will then, however, be contaminated by compounds not further defined, which are caused by the impurities in the starting material. However, since in a number of applications of orthisilicic acid tetraalkoxyalkyl esters the purity of the product is of secondary importance (e.g., in the case of binding agents for heavily pigmented paints), one can advantageously use ferrosilicon or iron silicide.

The silicon or silicon alloy grain fineness is not to be too coarse, because the speed of the reaction diminishes as the grain size increases. The grain size is therefore to be under 50 microns, insofar as possible.

The reaction is performed preferably under normal pressure. The temperature limits stated therefore apply to normal pressure. The distillation of the alkoxyalkyl ester that forms, however, is preferably performed under a vacuum. If it is desired to remove the ester continuously, the entire reaction may also be performed in vacuo. However, this expensive procedure will be selected only if it is desired to exceed the upper temperature limit intentionally. This may be the case, for example, if ferrosilicon or silicon alloys are used as metallic starting components and it is not desired to have as impurities in the orthosilicic acid tetraalkoxyalkyl ester the byproducts which form when these starting products are used.

The process can also be conducted under pressure say 1 to 10 atmospheres. In that case, however, care should be taken to conduct the reaction within the stated temperature range for the production of pure products.

The reaction is catalyzed by small amounts of the corresponding ether alcoholate. The amount of ether alcoholate in the reaction mixture is preferably between 2 and 5 weight percent with reference to the total amount of liquid. The reaction, however, will also take place with smaller amounts of alcoholate. The alkali alkoxyalcoholate is preferably produced by the addition of alkali metal to the reaction mixture, consisting of the end product, the ether alcohol involved, and metallic silicon. However, a corresponding amount of the ether alcoholate may be added to the mixture in solid form or in the form of a solution in the corresponding ether alcohol.

The catalytic action of the alcoholate takes place only in solution. Under the reaction conditions of the invention, small percentages of the alcoholate will always be in solution, since they are very easily soluble in the ether alcohols, but less soluble in the silicic acid esters. Therefore, the process can be conducted using alcoholate in solid form especially where a greater amount of silicic acid ester and alkali alcoholate be present. As soon as more ether alcohol is added, a portion of the alcoholate dissolves and the reaction starts spontaneously.

The speed of the reaction depends on the amount of ether alcohol charged to the reaction mixture, and therefore the process can be precisely controlled by the rate of feed of the reacting ether alcohol. When the ether alcohol feed is interrupted, the reaction soon ends as the ether alcohol still in the reactor is consumed. The entire heat requirements can be supplied by the exothermic heat of formation (reaction). Hence, the rate of ether alcohol addition must be such that the heat generated does not raise the reaction temperature above 250° C.

Ether alcohols which are suitable for use in accordance with the invention are both the monoalkyl ethers which can be derived from ethylene glycol and those which can be derived from diethylene or triethylene glycol, the alkyl group amounting to from 1 to 8 and preferably 1 to 4 carbon atoms. Examples of the first-named group of compounds are 2-methoxyethanol, 2-ethoxyethanol and 2-propoxyethanol. The second group includes, for example, methyldiglycol, ethyldiglycol and butyldiglycol. Other monoalkyl ether alcohols which can be used to form the corresponding ester are:

The process of the invention is preferably performed by suspending or dissolving all of the silicon and the amount of alkali metal, preferably sodium, that is required for the formation of the ether alcoholate, in a vessel containing the desired orthosilicic acid tetraalkoxyalkyl ester. Then the ether alcohol is added, whereupon first the corresponding alcoholate forms, and then the desired ester.

The process can also be performed by adding silicon and ether alcohol separately at the same time to a mixture of the desired ester and the alkali metal, the silicon being added, as a further variant, in the form of a suspension in the desired end product. In the latter case it is recommendable to carry the end product in a secondary circuit.

The orthosilicic acid tetraalkoxyalkyl esters obtained by the present process are used increasingly as binding agents for zinc dust paints. They are also used for binding molding sands in foundry practice.

In order to more fully illustrate the nature of the invention and the manner of practicing the same, the following examples are presented.

EXAMPLE 1

A two-liter glass vessel with stirrer, equipped with an insulated still, an infeed connection and a device for measuring the temperature in the liquid (thermocouple) was charged with 500 g of orthosilicic acid-2-methoxyethyl ester, which had previously been obtained by transesterification of orthosilicic acid tetramethyl ester with 2-methoxyethanol, plus 250 g of silicon (98% Si, 10μ diam.) and 9 g of sodium. After removal of the air from the reaction vessel by means of dry nitrogen, the vessel was heated with stirring at 150° C. After the addition of about 50 ml. of 2-methoxyethanol, a slight yielding of $H_2$ occured at first, due to the reaction of the metallic sodium; then, as the addition of 2-methoxyethanol continued, the $H_2$ development increased to 200 liters per hour. During the reaction no external heating was necessary, and the temperature could be maintained at 150° C. due to the exothermic heating effect.

After the distillation of 1 kg. of 2-methoxyethanol over a period of 40 minutes the feed was shut off, the development of hydrogen gas ending within a few minutes.

Under a vacuum of 0.1 Torr, 1085 g of orthosilicic acid tetra-2-methoxyethyl ester was obtained at 145° C. in a purity of 99.5%. With respect to the amount of alcohol used and the amount of hydrogen formed, the reaction corresponded to a volume-time yield of about 750 grams per liter per hour.

EXAMPLE 2

250 g of silicon (98% Si, 10μ diam.), 8 g of sodium, and 500 g of orthosilicic acid-2-ethoxyethanol previously obtained from the transesterification of orthosilicic acid tetramethyl ester with 2-ethoxyethanol were charged into the same apparatus as in Example 1. The mixture was heated to approximately 150° C. with stirring, after the reaction chamber was flooded with nitrogen, and 2-ethoxyethanol was fed into it in accordance with the amount of hydrogen evolved.

The reaction mixture becomes warmer due to the exothermic production of heat by the reaction. At 185° C., a total of 1 kg. of 2-ethoxyethanol was fed in over a 30 minute period, while at the same time approximately 130 liters of $H_2$ were formed. When the feed was shut off, the $H_2$ formation also ended a few minutes later.

At a vacuum of 0.1 Torr and a temperature of 158° C., 1280 g of orthosilicic acid tetra-2-ethoxyethyl ester was drawn off having a purity of 98.4%.

With respect to the alcohol put in and the hydrogen that was formed, the reaction corresponded to a volume-time yield of approximately 1150 grams per liter per hour.

EXAMPLE 3

The procedure was similar to that of Example 2 except that the reaction was performed at 230° C.

The volume-time yield was substantially higher than in Example 2, but the product purity fell below 90%.

EXAMPLE 4 (COMPARATIVE EXAMPLE)

The procedure was similar to that of Example 2 except that the reaction was performed at 120° C.

The volume-time yield dropped to 1/10 of that of Example 2.

EXAMPLE 5

250 g of silicon (98% Si, 10μ), 6 g of sodium and 500 g of orthosilicic acid-2-butoxyethanol previously obtained by the transesterification of orthosilicic acid tetramethyl ester with 2-butoxyethanol, were placed in the same apparatus as in Example 1. After the reaction chamber was flooded with nitrogen, the mixture was heated with stirring to about 200° C., and 2-butoxyethanol was slowly fed in until the sodium had reacted away.

At a reaction temperature of 200° to 210° C., a total of 1090 g of 2-butoxyethanol was fed in over a period of 30 minutes and approximately 100 liters of $H_2$ were formed. After the feed was shut off, the formation of $H_2$ also ended within a few minutes.

At a vacuum of 1 Torr and a temperature of 200° to 210° C., 1142 g of orthosilicic acid tetra-2-butoxyethyl ester was distilled out with a purity of 97.5%. With respect to the hydrogen that was formed, the reaction corresponded to a volume-time yield of approximately 1145 g/liter/hour.

EXAMPLE 6

250 g of silicon (98% Si, 10μ), 5 g of sodium and 500 g of orthosilicic acid tetraethyl diglycol ester previously obtained by transesterifying silicic acid tetramethyl ester with diethylene glycol monoethyl ether, were placed in the same apparatus as in Example 5.

After the reaction vessel had been flooded with nitrogen, the mixture was heated with stirring to about 210° C., and first the sodium was reacted away by the addition of diethylene glycol monoethyl ether.

At 210° C., a total of 970 g of diethylene glycol monoethyl ether was added over a period of 40 minutes, 80 liters of $H_2$ being formed.

After termination of the alcohol feed, the evolution of $H_2$ also terminated a few minutes later.

At a vacuum of 0.5 Torr and a temperature of 230° to 240° C., 1030 g of orthosilicic acid tetraethyl diglycol ester was drawn off with a purity of 86%.

With respect to the amount of hydrogen formed, the reaction corresponded to a volume-time yield of 770 grams per liter per hour.

If prior to the evaporation of the reaction product the solids (unreacted silicon, alcoholates etc.) are separated from the reaction mixture, by filtration or centrifugation, for example, esters of greater purity are obtained upon distillation.

What is claimed is:

1. A process for preparing an orthosilicic acid tetra-ester of a monoalkyl ether of an aliphatic glycol having 2 to 6 carbon atoms which comprises contacting silicon, iron silicide or ferrosilicon with a monoalkyl ether of an aliphatic glycol having 2 to 6 carbon atoms in the first alcohol chain in the presence of the corresponding orthosilicic acid tetraalkoxy alkyl ester present in an amount of 70 to 99 weight percent, based upon the total amount of liquid in the reaction vessel at a temperature between 125° and 250° C.

2. A process according to claim 1 wherein to a reaction vessel containing orthosilicic acid tetraalkoxy alkyl ester there is added silicon, iron silicide or ferrosilicon, the corresponding ether-alcohol of said ester, and an alkali metal ether alcoholate of said alcohol.

3. A process according to claim 1 wherein said alkali metal alcoholate is a sodium alcoholate.

4. A process according to claim 1 wherein said ester is orthosilicic acid tetra-(2-methoxyl ethyl)-ester and said ether is 2-methoxyethanol, the process is carried out at 140° to 190° C. using silicon having a purity of greater than 98%.

5. A process according to claim 1 wherein said ester is orthosilicic acid tetra-(2-ethoxyethyl)-ester and said ether is 2-ethoxyethanol, the process is carried out at 140° to 190° C. using silicon having a purity of greater than 98%.

6. A process according to claim 1 wherein said ester is an orthosilicic acid tetra-(alkyl-diglycol)-ester whose alkyl radical has 1–4 carbon atoms and the process is carried out at a temperature between 190° and 250° C.

7. A process according to claim 1 wherein said ester is orthosilicic acid tetra-(2-propoxylethyl)-ester, the ether is 2-propoxyethanol and the process is carried out at a temperature between 180° and 225° C. using silicon of purity greater than 98%.

8. A process according to claim 1 wherein said ester is orthosilicic acid tetra-(2-butoxyethyl)-ester, the ether is 2-butoxyethanol and the process is carried out at a temperature between 180° and 225° C. using silicon of purity greater than 98%.

9. A process according to claim 1 wherein the reactants are present in the following weight percent amounts:

silicon, iron silicide or ferrosilicon 1 to 80
monoalkyl ether of aliphatic glycol 1 to 30.

10. A process according to claim 1 wherein the following reactants are present in the following weight percent amounts:

silicon, iron silicide or ferrosilicon 1 to 80
alkali metal ether alcoholate 0.4 to 5.

11. A process according to claim 1 wherein to a reaction vessel containing orthosilicic acid tetraalkoxyalkyl ester, alkali metal and silicon, iron silicide or ferrosilicon there is added the corresponding monoalkyl ether alcohol.

* * * * *

UNITED STATES PATENT AND TRADEMARK OFFICE
CERTIFICATE OF CORRECTION

PATENT NO. : 4,197,252
DATED : April 8, 1980
INVENTOR(S) : WILHELM JOCH, ARNOLD LENZ, WALTER ROGLER It is certified that error appears in the above-identified patent and that said Letters Patent are hereby corrected as shown below:

Column 2, line 65, Figures should be --20 to 98-- and --35 to 55--.

Signed and Sealed this

Twenty-ninth Day of July 1980

[SEAL]

Attest:

SIDNEY A. DIAMOND

Attesting Officer

Commissioner of Patents and Trademarks